United States Patent [19]

Alftine

[11] 4,455,861
[45] Jun. 26, 1984

[54] MOLECULAR SIEVE OXYGEN MONITOR

[75] Inventor: David N. Alftine, Bettendorf, Iowa

[73] Assignee: Litton Systems, Inc., Davenport, Iowa

[21] Appl. No.: 460,305

[22] Filed: Jan. 24, 1983

[51] Int. Cl.³ ............................................. G01N 31/06
[52] U.S. Cl. .............................................. 73/23; 55/21
[58] Field of Search .......... 73/23; 128/202.26, 204.18, 128/204.22, 205.12; 55/21, 25, 26, 58

[56] References Cited

U.S. PATENT DOCUMENTS 3,922,149 11/1975 Ruder et al. ............................ 55/21
4,428,372 1/1984 Beysel et al. ............................ 55/21

FOREIGN PATENT DOCUMENTS 2029257 3/1980 United Kingdom ..................... 55/21

Primary Examiner—Stephen A. Kreitman
Attorney, Agent, or Firm—Brian L. Ribando

[57] ABSTRACT

A monitoring system for determining the concentration of oxygen in the product gas of an oxygen enriching system includes differential pressure regulator means for reducing the pressure of the product gas, for regulating the pressure of the product gas at a preset level, and for referencing the regulated pressure to atmospheric pressure. Solenoid valves allowing product gas to pressurize the monitoring system in a first condition and to allow product gas to vent the monitoring system to the atmosphere in a second condition are also included. Restrictive orifices upstream and downstream of a bed of molecular sieve material eliminate pressure spikes in the monitoring system. A bed of molecular sieve material to adsorb oxygen from the product gas wherein, in a first condition, with the system pressurized, the upper pressure limit is attenuated as the molecular sieve bed absorbs oxygen from the product gas, and, in a second condition, with the system vented to the atmosphere, the lower pressure limit is attenuated by the rate of desorption of the oxygen from the molecular sieve bed. Further included is a pressure transducer with means for converting the system pressure to an electrical analog of that pressure including means for comparing the electrical analog to a reference and inferring oxygen concentration.

4 Claims, 2 Drawing Figures

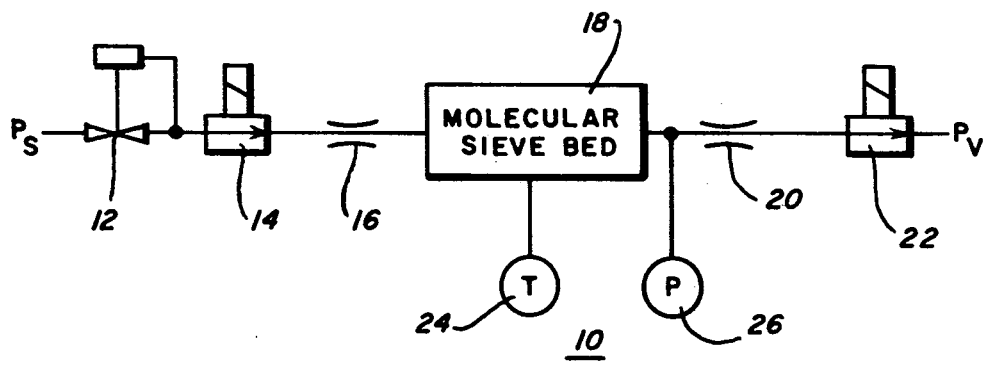
Fig_1
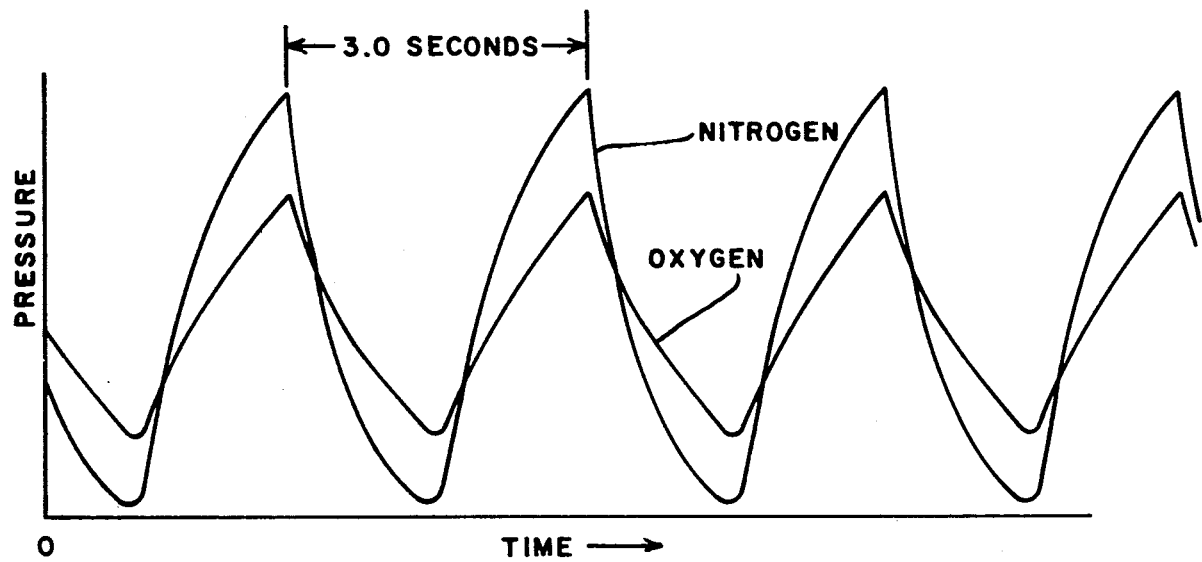
Fig_2

MOLECULAR SIEVE OXYGEN MONITOR

BACKGROUND OF THE INVENTION

Oxygen enriched breathing systems such as are found in hospitals and aircraft use as oxygen sources bottled high pressure gas, liquid oxygen, solid oxygen generators, commonly referred to as "candles", or fractionalized air. It can become critical that the user know the oxygen concentration in the breathing system to avoid a catastrophic event such as could occur in high alitude aircraft.

Air fractionalizing is normally accomplished by alternating the flow of high pressure air through each of two beds of molecular sieve material such as a zeolite. This process is identified as the pressure swing adsorption technique. Systems employing this technique can be made to produce either a nitrogen or an oxygen enriched effluent based on the type of zeolite chosen. Some zeolites adsorb oxygen and others nitrogen. In an oxygen enriching system, a zeolite which adsorbs nitrogen would be selected.

These same adsorption characteristics of a zeolite can be used in monitoring the effluent concentrations of product gas from an air fractionalizing system or any other source.

SUMMARY AND OBJECTS OF THE INVENTION

According to the invention, a molecular sieve oxygen monitor is used to determine the oxygen concentration of the product gas of an oxygen enriching system through the application of a bed of molecular sieve material such as zeolite to adsorb oxygen from samples of the system effluent.

Though the description of the monitor focuses principally on oxygen enriching systems, it is understood that the monitor applies equally to nitrogen enriching system or any other enriched product gas for which a suitable absorber exists.

It is therefore an object of this invention to provide a monitor for determining the oxygen concentration of the product gas of an oxygen enriching system.

It is another object of this invention to provide a monitor which continuously samples the product gas to monitor oxygen concentration.

It is still further an object of this invention to provide a monitor which functions independent of product gas system pressure and ambient pressure, altitude in the case of aircraft.

BRIEF DESCRIPTION OF THE DRAWINGS

FIG. 1 is a schematic representation of a molecular sieve oxygen monitor according to the invention.

FIG. 2 is a pressure swing profile of the molecular sieve oxygen monitor of FIG. 1 illustrating the variation in pressure excursions between oxygen and nitrogen enriched product gas.

DETAILED DESCRIPTION OF THE PREFERRED EMBODIMENT

Referring to FIG. 1, the molecular sieve oxygen monitor 10 includes a differential pressure regulator 12 which regulates the pressure of the effluent gas samples $P_s$ from an oxygen enriching supply (not shown). The differential pressure regulator 12 references its output pressure to the atmospheric pressure and maintains a constant differential thereto. In applications where the atmospheric pressure can vary, such as in aircraft, the constant differential pressure establishes a reference system flow-through rate from which the nitrogen or oxygen concentrations of the effluent gas can be inferred as more fully explained below.

The gas flow from the regulator 12 is controlled by an input solenoid valve 14 which is driven by an electrical timing circuit (not shown), which circuit holds the solenoid valve open for a first period of 1.5 seconds of a 3.0 second sampling cycle time. In order to prevent pressure spikes, a restrictive orifice 16 allows for a gradual system pressure increase over the 1.5 seconds when the input solenoid valve 14 is open.

The effluent sample flows through a bed 18 of molecular sieve material and on through a restrictive orifice 20 to an output solenoid valve 22. The ouput solenoid 22 is held closed for the first period of 1.5 seconds and is opened for a second period of 1.5 seconds of the 3 second sampling time cycle. During this second 1.5 second period, the input solenoid valve 14 is held closed.

The temperature of the molecular sieve bed 18 is monitored by a temperature transducer 24. The output of the transducer 24 is used to either control the temperature of the bed 18 or to correct the system pressure output readings. A pressure transducer 26 converts the pressure of the oxygen monitor 10 to an electrical signal which is fed to a signal conditioner (not shown). The signal conditioner interprets the system pressure swing limits from which oxygen concentrations are inferred and displayed.

MODE OF OPERATION OF THE PREFERRED EMBODIMENT

To start the oxygen monitor 10, a timing circuit (not shown) is activated, and alternately, electrically excites the solenoid valves 14 and 22 for 1.5 second periods holding the first open while the second is closed and closing the first when the second is open.

The pressure of the gas sample $P_s$ is reduced to a preset level by the regulator 12. The regulated pressure is referenced to the atmospheric pressure maintaining a constant differential pressure across the monitor 10 from the source $P_s$ to the system vent $P_v$. When the solenoid valve 14 is cycled open for 1.5 seconds, the monitor 10 pressure is gradually increased as the gas flows through the restrictive orifice 16. With the solenoid valve 22 closed during this first 1.5 second period, the pressure in the monitor 10 reaches a level proportional to the adsorptive capabilities of the molecular sieve material in the bed 18. If the product gas is oxygen-rich and a molecular sieve material which adsorbs oxygen, such as a zeolite 4A, is selected, the upper pressure limit attained in the system will be less than that which would be attained by a nitrogen-rich gas or by air as the oxygen is adsorbed.

As the system vents through the restrictive orifice 20 to the atmosphere when the solenoid valve 22 opens and the valve 14 closes in the second 1.5 second period, the lower pressure limit reached by the monitor 10 will be decreased as a function of the rate of desorption of the sieve material in bed 18. Both the upper and lower limit pressure attenuation of an oxygen-rich product gas acting through a monitor whose bed 18 is charged with a molecular sieve material, such as a zeolite 4A which readily adsorbs oxygen, are illustrated in FIG. 2. FIG. 2 also illustrates the pressure swing of air or any nitrogen-rich gas flowing through that same system using a zeolite 4A.

The calibration of the monitor 10 includes establishing a correlation between the pressure swing of nitrogen and that of oxygen in an oxygen adsorbing system. The pressure transducer 26 provides an electrical signal which is an analog of the monitor 10 system pressure. This electrical signal is compared to an equivalent signal for the reference gas, in this example, nitrogen, and an oxygen concentration is inferred. Should the temperature of the bed change from that at which the monitor 10 was calibrated, a correction is applied to the inferred concentration level.

It is clear that this molecular sieve adsorptive technique is equally applicable to any enriched product gas for which an adsorber is available for the enriching component of that gas.

What is claimed is:

1. A monitoring system for determining the concentration of oxygen in the product gas of an oxygen enriching system comprising:
    a differential pressure regulator means for reducing the pressure of said product gas, and for regulating the pressure of said product gas at a preset level, and for referencing said regulated presssure to atmospheric pressure,
    solenoid valves for allowing product gas to pressurize said monitoring system in a first condition and to allow product gas to vent the monitoring system to the atmosphere in a second condition,
    restrictive orifices upstream and downstream of a bed of molecular sieve material to eliminate pressure spikes in said monitoring system,
    a bed of molecular sieve material to adsorb oxygen from said product gas which
    in a first condition, with the system pressurized, the upper pressure limit is attenuated as the molecular sieve bed adsorbs oxygen from the product gas, and
    in a second condition, with the system vented to the atmosphere, the lower pressure limit is attenuated by the rate of desorption of the oxygen from the molecular sieve bed, and
    a pressure transducer with means for converting the system pressure to an electrical analog of that pressure including means for comparing said electrical analog to a reference and inferring oxygen concentration.

2. A monitoring system for determining the concentration of any particular gas in a system for producing a product gas enriched in that particular gas comprising:
    a differential pressure regulator means for reducing the pressure of said product gas, and for regulating the pressure of said product gas at a preset level and for referencing said regulated pressure to atmospheric pressure,
    solenoid valves for allowing product gas to pressurize said monitoring system in a first condition and to allow product gas to vent the monitoring system to the atmosphere in a second condition,
    restrictive orifices upstream and downstream of a bed of molecular sieve material to eliminate pressure spikes in said monitoring system,
    a bed of molecular sieve material to adsorb said particular gas from said product gas which
    in a first condition, with the system pressurized, the upper pressure limit is attenuated as the molecular sieve bed adsorbs particular gas from the product gas, and
    in a second condition, with the system vented to the atmosphere, the lower pressure limit is attenuated by the rate of desorption of the particular gas from the molecular sieve bed, and
    a pressure transducer with means for converting the system pressure to an electrical analog of that pressure including means for comparing said electrical analog to a reference and inferring the particular gas concentration.

3. A monitoring system as recited in claim 1, wherein the temperature of said molecular sieve bed is monitored and is compensated to maintain the bed temperature constant.

4. A monitoring system as recited in claim 1, wherein the temperature of said molecular sieve bed is monitored and is used to generate a correction to said electrical analog means.